US00PP10257P

United States Patent [19]

Cosner et al.

[11] Patent Number: Plant 10,257

[45] Date of Patent: Feb. 24, 1998

[54] DOUBLE IMPATIENS PLANT NAMED 'TIOGA RED'

[76] Inventors: Harlan B. Cosner; Sue L. Cosner, both of P.O. Box 173, Broadbent, Oreg. 97414

[21] Appl. No.: 772,492

[22] Filed: Dec. 23, 1996

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—C. A. Whealy

[57] ABSTRACT

A new and distinct cultivar of Double Impatiens plant named 'Tioga Red', characterized by its large purple red flowers; flowers held above or beyond the foliage; consistently double and symmetrical flower form; numerous flowers per plant; freely branching, dense plant habit; upright and slightly arching plant habit, triangular in shape; and dark green foliage.

1 Drawing Sheet

The present invention relates to a new and distinct cultivar of Double Impatiens plant, botanically known as *Impatiens walleriana*, and hereinafter referred to by the cultivar name 'Tioga Red'.

The new cultivar is a spontaneous mutation of a unnamed proprietary seedling selection. The new cultivar was discovered and selected by the inventors in a controlled environment in Coquille, Ore., in July, 1991, as a single lateral branch of a plant of the unnamed proprietary seedling selection. This single lateral branch was chosen as it produced fully double flowers. Asexual reproduction of the new cultivar by terminal cuttings taken at Coquille, Ore., has shown that the unique features of this new Double Impatiens are stable and reproduced true to type in successive generations of asexual reproduction.

The following traits have been repeatedly observed and are determined to be the unique characteristics of 'Tioga Red'. These characteristics in combination distinguish the new Double Impatiens as a new and distinct cultivar:

1. Large purple red flowers.
2. Flowers held above or beyond the foliage.
3. Consistently double and symmetrical flower form.
4. Numerous flowers per plant.
5. Freely branching, dense plant habit.
6. Upright and slightly arching plant habit, triangular in shape.
7. Dark green foliage.

In contrast to plants of the new Double Impatiens, plants of the parent proprietary seedling selection had semi-double flowers with reproductive organs and capable of producing seed.

The new Double Impatiens is similar in flower color to the Double Impatiens cultivar Rosebud Red (not patented). However in side-by-side comparisons in Coquille, Ore., under commercial practice, plants of the new Double Impatients differed from plants of the cultivar Rosebud Red in the following characteristics:

1. Plants of the new Double Impatiens are taller and more vigorous than plants of the cultivar Rosebud Red.
2. Plants of the new Double Impatiens are upright and triangular in shape whereas plants of the cultivar Rosebud Red cascade downwards.
3. Plants of the new Double Impatiens are more freely branching and are denser than plants of the cultivar Rosebud Red.
4. Leaves of plants of the new Double Impatiens are longer and narrower with longer petioles than leaves of plants of the cultivar Rosebud Red.
5. Flowers of plants of the new Double Impatiens face upward or outward whereas flowers of plants of the cultivar Rosebud Red face outward or downward as peduncles of plants of the cultivar Rosebud Red are weaker than peduncles of the new Double Impatiens.
6. Flowers of the new Double Impatiens are smaller than flowers of the cultivar Rosebud Red.

A detailed comparison of plants of the new Double Impatiens and the cultivar Rosebud Red appears in Chart A at the end of the specification .

The new Double Impatines has not been observed under all possible environmental conditions. The phenotype may vary significantly with variations in environment such as temperature and light level, without, however, any variance in genotype.

The accompanying colored photographs illustrate the overall appearance and flower color of the new Double Impatiens, showing the colors as true as it is reasonably possible to obtain in colored reproductions of this type.

The first photograph comprises a side perspective view of a typical plant of the new Double Impatiens.

The second photograph comprises a side perspective view of typical plants of the cultivar Rosebud Red (left) and the new Double Impatiens (right) showing the differences in plant and flowering habit. Flower and foliage colors in the photographs may appear different from the actual colors due to light reflectance.

The following observations, measurements, values and comparisons describe plants grown in Coquille, Ore., grown under double layer of polyethylene with day temperatures ranging from 23 to 30C and night temperatures ranging from 10 to 18C, and light levels ranging from 3,000 to 5,000 footcandles.

In the following description, color references are made to The Royal Horticultural Society Colour Chart except where general terms of ordinary dictionary significance are used.

Botanical classification: *Impatiens walleriana* cultivar 'Tioga Red'.

Parentage: Spontaneous mutation of a unnamed proprietary seedling selection.

Propagation:

*Type cutting.*—Terminal cuttings.

*Time to initiate roots.*—About 14 days at a temperature of 20C.

*Rooting habit.*—Numerous, fibrous, and well-branched.

Plant description:

*Form.*—Upright and slightly arching, triangular in shape.

*Growth habit.*—Vigorous. Dense and bushy growth. Flowers above or beyond the foliage. Suitable for 10 to 25-cm containers.

*Plant height.*—About 33 cm.

*Branching habit.*—Freely branching with about eight lateral branches, branches strong.

*Lateral branches.*—Size: Length: About 27 cm. Diameter: About 1 cm. Internode length: About 3.3 cm. Color: 147B, translucent with red, 59A, spots.

*Foliage description.*—Leaves simple, generally symmetrical, abundant, alternate, and flat in aspect. Size, largest leaves: Length: About 6 cm. Width: About 3.25 cm. Shape: Ovate with acuminate apex, attenuate base and crenate margin. Texture: Smooth. Color: Upper surface: 147A. Lower surface: 147B with red (close to 183D) blotches. Venation, upper surface: 147B. Venation, lower surface: 147B. Petiole: Size: Length: About 3 cm. Diameter: About 2 mm. Color: White.

Flower description:

*Flower type and habit.*—Large purple red flowers. Consistently double and symmetrical flowers. Freely and continuously flowering. Flower buds open similar to a rose in fullness. Flowers arise from leaf axils, terminal bud opening first. Usually six to eight flowers per lateral branch. Flowers positioned above or beyond the foliage and face upward or outward. Flowers self-cleaning.

*Time to flower.*—Flowering generally commences four to six weeks after planting.

*Flowering season.*—Year-round under greenhouse conditions. In the garden, flowering is continuous from spring until fall.

*Flower diameter.*—About 3.5 cm.

*Flower depth (height).*—About 1.5 cm.

*Flower buds.*—Size: Length: About 1.4 cm. Diameter: About 1 cm. Shape: Ovoid. Color: 50B.

*Petals/petaloids.*—Quantity: Numerous. Size (largest petals): Length: About 1.7 cm. Width: About 1.8 cm. Shape: Round with rounded apex, cuneate or obtuse base and entire margin. Texture: Velvety, smooth. Color: When opening, upper surface: Iridescent, 60B. When opening, lower surface: Iridescent, 50B. Mature, upper surface: Iridescent, 60B. Mature, lower surface: Iridescent, 50B. Fading to: Iridescent, 60B.

*Spur.*—Length: About 2.7 cm. Shape: Narrow and curved. Color: Light green with reddish overtones.

*Peduncles.*—Length: About 2.5 cm. Angle: Upright to outwardly arching. Strength: Moderate. Color: 145B.

*Reproductive organs.*—None observed. Under optimal flowering conditions, reproductive organs are not observed as these structures develop into sterile petaloids. Without the development of functional reproductive organs, pollination and subsequent seed production are not observed.

Disease resistance: Under commercial conditions, resistance nor susceptibility to pathogens has not been observed.

CHART A

| CHARACTERISTIC | 'TIOGA RED' | 'ROSEBUD RED' |
|---|---|---|
| GROWTH HABIT | Upright, slightly arching, triangular | Initially upright, then cascading downward |
| PLANT HEIGHT | About 33 cm | About 17 cm |
| VIGOR | Vigorous | Moderate |
| BRANCHING HABIT | Freely, usually 8 lateral branches per plant, dense | Low to moderate, usually 5 lateral branches per plant, less dense |
| LATERAL BRANCH DIAMETER | About 1 cm | About 8 mm |
| LATERAL BRANCH STRENGTH | Strong | Weak |
| LEAF LENGTH | About 6 cm | About 5.5 cm |
| LEAF WIDTH | About 3.25 cm | About 3.5 cm |
| PETIOLE LENGTH | About 3 cm | About 2.5 cm |
| FLOWERING HABIT | Flowers face upward or outward | Flowers face outward or downward |
| QUANTITY OF FLOWERS PER LATERAL BRANCH | 6 to 8 | 5 to 8 |
| FLOWER DIAMETER | About 3.5 cm | About 4 cm |
| PEDUNCLE ANGLE | Upright to outwardly arching | Outwardly arching to downward |
| PEDUNCLE STRENGTH | Moderate | Weaker |

It is claimed:

1. A new and distinct Double Impatiens plant named 'Tioga Red', as illustrated and described.

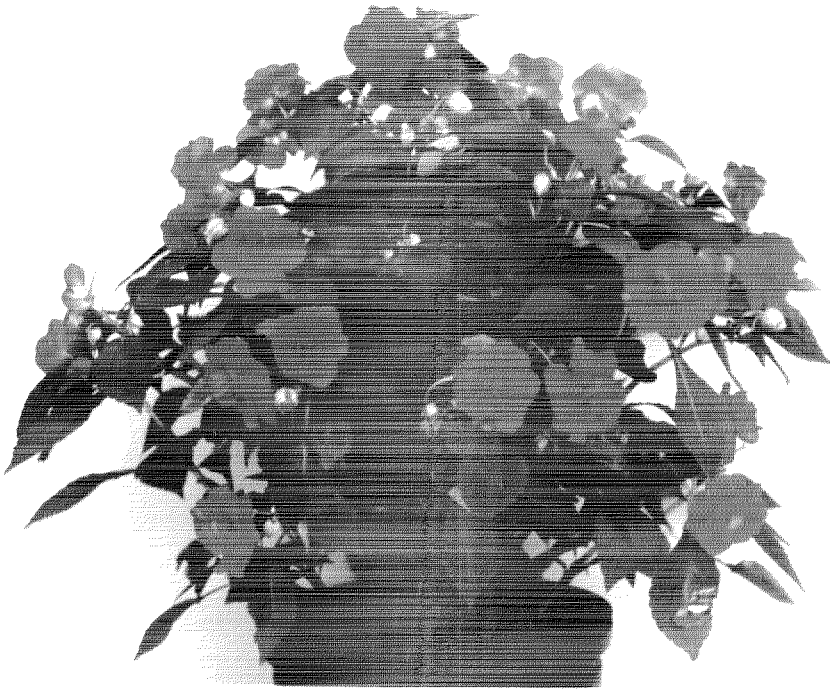
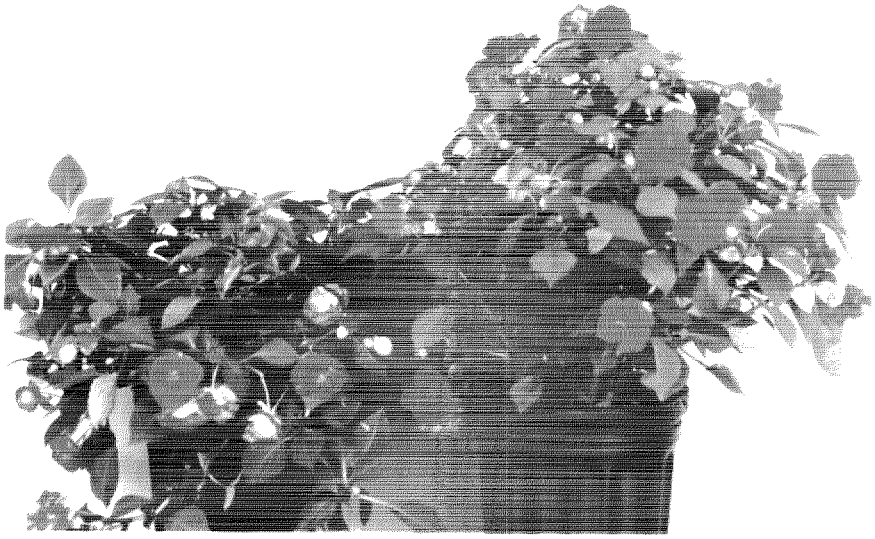

* * * * *